(12) United States Patent
Buchholz et al.

(10) Patent No.: US 7,429,452 B2
(45) Date of Patent: Sep. 30, 2008

(54) METHODS FOR DIAGNOSIS AND THERAPY OF PANCREATIC CANCER AND COMPOSITION USEFUL THEREIN

(75) Inventors: Malte Buchholz, Lonsee (DE); Thomas Gress, Elchingen (DE); Stephanie Loesch, Penzberg (DE); Ulrich Weidle, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 486 days.

(21) Appl. No.: 10/696,487

(22) Filed: Oct. 29, 2003

(65) Prior Publication Data

US 2004/0110219 A1    Jun. 10, 2004

(30) Foreign Application Priority Data

Oct. 31, 2002    (EP) .................................. 02024539

(51) Int. Cl.
*C12Q 1/68* (2006.01)
*C12Q 1/00* (2006.01)
*C07H 21/02* (2006.01)

(52) U.S. Cl. ............................................. 435/6; 435/4

(58) Field of Classification Search ....................... None
See application file for complete search history.

(56) References Cited

U.S. PATENT DOCUMENTS 5,912,143 A * 6/1999 Bandman et al. ........... 435/69.1
2002/0081659 A1   6/2002 Rosen et al.

FOREIGN PATENT DOCUMENTS

EP         0279 669       8/1988
WO       WO 02/08288      1/2002

OTHER PUBLICATIONS

Pollack et al (Nature Genetics, 1999, 23:41-46).*
Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
Stites et al (Basic and Clinical Immunology, 7th Ed., Appleton and Lange, Norwalk, 1991, p. 260).*

* cited by examiner

*Primary Examiner*—Susan Ungar
(74) *Attorney, Agent, or Firm*—George W. Johnston; Patricia S. Rocha-Tramaloni; Gene J. Yao (57) ABSTRACT

Polynucleotide and polypeptide UKW are specific for pancreatic tumors. Diagnosis of UKW is therefore valuable for diagnosis of pancreatic tumors. Antibodies against UKW are, besides their value in diagnosis, useful as therapeutic agents for the treatment of pancreatic tumors.

5 Claims, 5 Drawing Sheets

Figure 2:
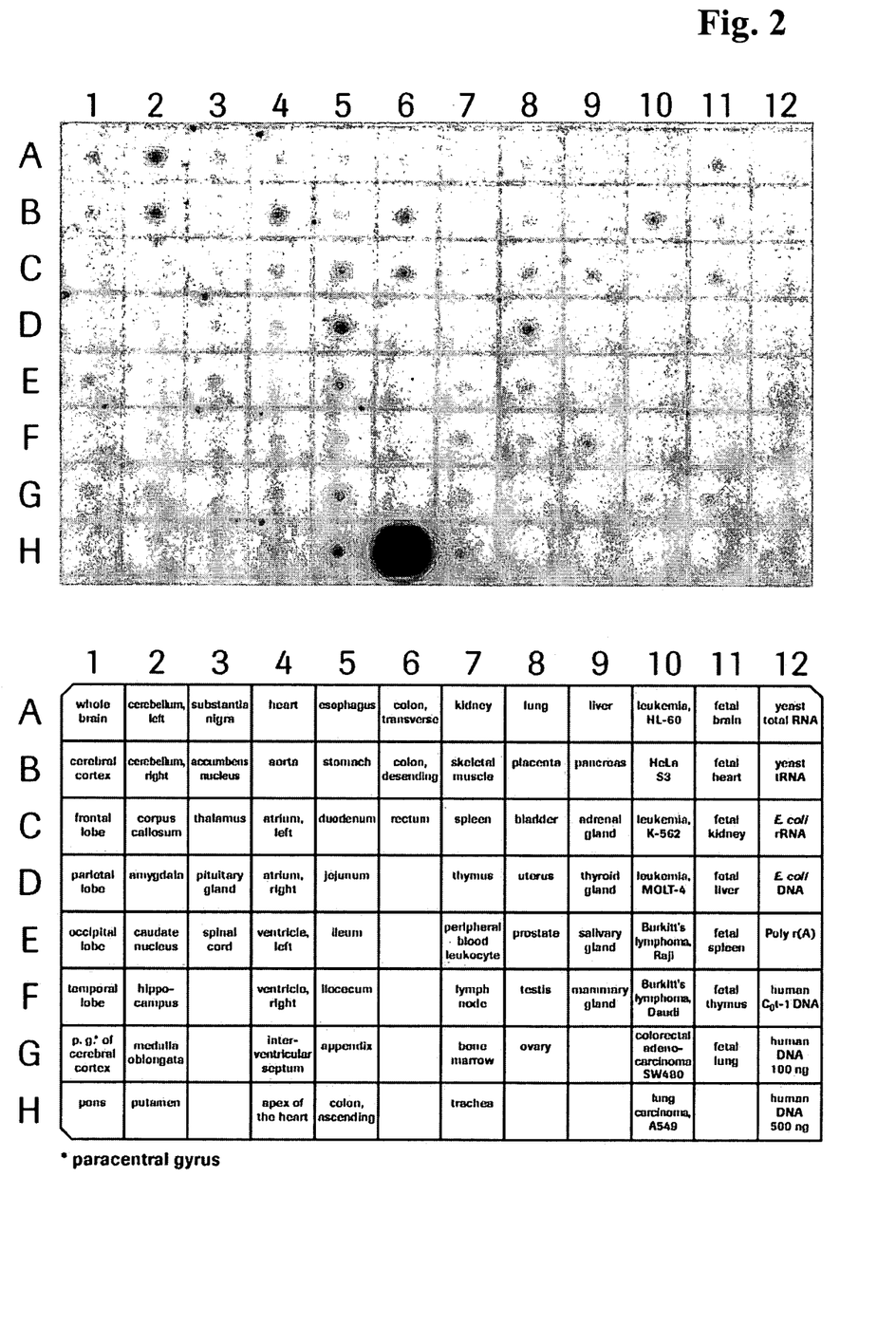
FIG. 2 Multiple Tissue Expression (MTE™) Array (Clontech, Palo Alto, Calif., USA). This array contains normalized loadings of poly $A^+$-RNA from 76 different tissues as well as control RNA's and DNA's and enables to screen for the presence and relative abundance of a target mRNA in a broad spectrum of fetal and adult tissues. H6 corresponds to 1 μg total RNA from pancreatic tumor cell line SUIT-2 007. The code is revealed below.

| | 1 | 2 | 3 | 4 | 5 | 6 | 7 | 8 | 9 | 10 | 11 | 12 |
|---|---|---|---|---|---|---|---|---|---|---|---|---|
| A | whole brain | cerebellum, left | substantia nigra | heart | esophagus | colon, transverse | kidney | lung | liver | leukemia, HL-60 | fetal brain | yeast total RNA |
| B | cerebral cortex | cerebellum, right | accumbens nucleus | aorta | stomach | colon, desending | skeletal muscle | placenta | pancreas | HeLa S3 | fetal heart | yeast tRNA |
| C | frontal lobe | corpus callosum | thalamus | atrium, left | duodenum | rectum | spleen | bladder | adrenal gland | leukemia, K-562 | fetal kidney | E. coli rRNA |
| D | parietal lobe | amygdala | pituitary gland | atrium, right | jejunum | | thymus | uterus | thyroid gland | leukemia, MOLT-4 | fetal liver | E. coli DNA |
| E | occipital lobe | caudate nucleus | spinal cord | ventricle, left | ileum | | peripheral blood leukocyte | prostate | salivary gland | Burkitt's lymphoma, Raji | fetal spleen | Poly r(A) |
| F | temporal lobe | hippo-campus | | ventricle, right | ilocecum | | lymph node | testis | mammary gland | Burkitt's lymphoma, Daudi | fetal thymus | human C₀t-1 DNA |
| G | p. g.* of cerebral cortex | medulla oblongata | | inter-ventricular septum | appendix | | bone marrow | ovary | | colorectal adeno-carcinoma SW480 | fetal lung | human DNA 100 ng |
| H | pons | putamen | | apex of the heart | colon, ascending | | trachea | | | lung carcinoma, A549 | | human DNA 500 ng |

* paracentral gyrus

SEQUENCE LISTING

```
<160> NUMBER OF SEQ ID NOS: 10

<210> SEQ ID NO 1
<211> LENGTH: 5120
<212> TYPE: DNA
<213> ORGANISM: Homo sapiens
<220> FEATURE:
<221> NAME/KEY: CDS
<222> LOCATION: (366)..(1484)

<400> SEQUENCE: 1
ggtaggaggc aaccatgtgg ttccagctga atttttttt tccctctctc tttcttcact      60 ccttttttctt tccaaacagg gaaaagtgtt ccacgaagcg gtagcgcctt tccgcctcgc     120
gttttcctcc ctgaccctgg tcccggctcc cgtccgggcg ccagctggtg gggcgagcgc     180
cgggagccca tctgccccca ggggcacggg gcgcggggcc ggctcccgcc cggcacatgg     240
ctgcagccac ctcgcgcgca ccccgaggcg ccgcgcccag ctcgcccgag gtccgtcgga     300
```

```
ggcgcccggc cgccccggag ccaagcagca gctgagcggg gaagcgcccg cgtccgggga      360 tcggg atg tcc ctc ctc ctt ctc ctc ttg cta gtt tcc tac tat gtt gga      410
      Met Ser Leu Leu Leu Leu Leu Leu Leu Val Ser Tyr Tyr Val Gly
      1               5                   10                  15 acc ttg ggg act cac act gag atc aag aga gtg gca gag gaa aag gtc        458
Thr Leu Gly Thr His Thr Glu Ile Lys Arg Val Ala Glu Glu Lys Val
                    20                  25                  30 act ttg ccc tgc cac cat caa ctg ggg ctt cca gaa aaa gac act ctg        506
Thr Leu Pro Cys His His Gln Leu Gly Leu Pro Glu Lys Asp Thr Leu
                35                  40                  45 gat att gaa tgg ctg ctc acc gat aat gaa ggg aac caa aaa gtg gtg        554
Asp Ile Glu Trp Leu Leu Thr Asp Asn Glu Gly Asn Gln Lys Val Val
            50                  55                  60 atc act tac tcc agt cgt cat gtc tac aat aac ttg act gag gaa cag        602
Ile Thr Tyr Ser Ser Arg His Val Tyr Asn Asn Leu Thr Glu Glu Gln
65                  70                  75 aag ggc cga gtg gcc ttt gct tcc aat ttc ctg gca gga gat gcc tcc        650
Lys Gly Arg Val Ala Phe Ala Ser Asn Phe Leu Ala Gly Asp Ala Ser
80              85                  90                  95 ttg cag att gaa cct ctg aag ccc agt gat gag ggc cgg tac acc tgt        698
Leu Gln Ile Glu Pro Leu Lys Pro Ser Asp Glu Gly Arg Tyr Thr Cys
                100                 105                 110 aag gtt aag aat tca ggg cgc tac gtg tgg agc cat gtc atc tta aaa        746
Lys Val Lys Asn Ser Gly Arg Tyr Val Trp Ser His Val Ile Leu Lys
            115                 120                 125 gtc tta gtg aga cca tcc aag ccc aag tgt gag ttg gaa gga gag ctg        794
Val Leu Val Arg Pro Ser Lys Pro Lys Cys Glu Leu Glu Gly Glu Leu
        130                 135                 140 aca gaa gga agt gac ctg act ttg cag tgt gag tca tcc tct ggc aca        842
Thr Glu Gly Ser Asp Leu Thr Leu Gln Cys Glu Ser Ser Ser Gly Thr
    145                 150                 155 gag ccc att gtg tat tac tgg cag cga atc cga gag aaa gag gga gag        890
Glu Pro Ile Val Tyr Tyr Trp Gln Arg Ile Arg Glu Lys Glu Gly Glu
160                 165                 170                 175 gat gaa cgt ctg cct ccc aaa tct agg att gac tac aac cac cct gga        938
Asp Glu Arg Leu Pro Pro Lys Ser Arg Ile Asp Tyr Asn His Pro Gly
                180                 185                 190 cga gtt ctg ctg cag aat ctt acc atg tcc tac tct gga ctg tac cag        986
Arg Val Leu Leu Gln Asn Leu Thr Met Ser Tyr Ser Gly Leu Tyr Gln
            195                 200                 205 tgc aca gca ggc aac gaa gct ggg aag gaa agc tgt gtg gtg cga gta        1034
Cys Thr Ala Gly Asn Glu Ala Gly Lys Glu Ser Cys Val Val Arg Val
        210                 215                 220 act gta cag tat gta caa agc atc ggc atg gtt gca gga gca gtg aca        1082
Thr Val Gln Tyr Val Gln Ser Ile Gly Met Val Ala Gly Ala Val Thr
    225                 230                 235 ggc ata gtg gct gga gcc ctg ctg att ttc ctc ttg gtg tgg ctg cta        1130
Gly Ile Val Ala Gly Ala Leu Leu Ile Phe Leu Leu Val Trp Leu Leu
240                 245                 250                 255 atc cga agg aaa gac aaa gaa aga tat gag gaa gaa gag aga cct aat        1178
Ile Arg Arg Lys Asp Lys Glu Arg Tyr Glu Glu Glu Glu Arg Pro Asn
                260                 265                 270 gaa att cga gaa gat gct gaa gct cca aaa gcc cgt ctt gtg aaa ccc        1226
Glu Ile Arg Glu Asp Ala Glu Ala Pro Lys Ala Arg Leu Val Lys Pro
            275                 280                 285 agc tcc tct tcc tca ggc tct cgg agc tca cgc tct ggt tct tcc tcc        1274
Ser Ser Ser Ser Ser Gly Ser Arg Ser Ser Arg Ser Gly Ser Ser Ser
        290                 295                 300
```

-continued

```
act cgc tcc aca gca aat agt gcc tca cgc agc cag cgg aca ctg tca      1322
Thr Arg Ser Thr Ala Asn Ser Ala Ser Arg Ser Gln Arg Thr Leu Ser
    305                 310                 315 act gac gca gca ccc cag cca ggg ctg gcc acc cag gca tac agc cta      1370
Thr Asp Ala Ala Pro Gln Pro Gly Leu Ala Thr Gln Ala Tyr Ser Leu
320                 325                 330                 335 gtg ggg cca gag gtg aga ggt tct gaa cca aag aaa gtc cac cat gct      1418
Val Gly Pro Glu Val Arg Gly Ser Glu Pro Lys Lys Val His His Ala
                340                 345                 350 aat ctg acc aaa gca gaa acc aca ccc agc atg atc ccc agc cag agc      1466
Asn Leu Thr Lys Ala Glu Thr Thr Pro Ser Met Ile Pro Ser Gln Ser
            355                 360                 365 aga gcc ttc caa acg gtc tgaattacaa tggacttgac tcccacgctt             1514
Arg Ala Phe Gln Thr Val
                370 tcctaggagt cagggtcttt ggactcttct cgtcattgga gctcaagtca ccagccacac    1574 aaccagatga gaggtcatct aagtagcagt gagcattgca cggaacagat tcagatgagc    1634 attttcctta tacaatacca aacaagcaaa aggatgtaag ctgattcatc tgtaaaaagg    1694 catcttattg tgcctttaga ccagagtaag ggaaagcagg agtccaaatc tatttgttga    1754 ccaggacctg tggtgagaag gttggggaaa ggtgaggtga atatacctaa aacttttaat    1814 gtgggatatt ttgtatcagt gctttgattc acaattttca agaggaaatg ggatgctgtt    1874 tgtaaatttt ctatgcattt ctgcaaactt attggattat tagttattca gacagtcaag    1934 cagaacccac agccttatta cacctgtcta caccatgtac tgagctaacc acttctaaga    1994 aactccaaaa aaggaaacat gtgtcttcta ttctgactta acttcatttg tcataaggtt    2054 tggatattaa tttcaagggg agttgaaata gtgggagatg gagaagagtg aatgagtttc    2114 tcccactcta tactaatctc actatttgta ttgagcccaa ataactatg aaaggagaca     2174 aaaatttgtg acaaaggatt gtgaagagct ttccatcttc atgatgttat gaggattgtt    2234 gacaaacatt agaaatatat aatggagcaa ttgtggattt cccctcaaat cagatgcctc    2294 taaggacttt cctgctagat atttctggaa ggagaaaata caacatgtca tttatcaacg    2354 tccttagaaa gaattcttct agagaaaaag ggatctagga atgctgaaag attacccaac    2414 ataccattat agtctcttct ttctgagaaa atgtgaaacc agaattgcaa gactgggtgg    2474 actagaaagg gagattagat cagttttctc ttaatatgtc aaggaaggta gccgggcatg    2534 gtgccaggca cctgtaggaa atccagcag gtggaggttg cagtgagcca agattatgcc     2594 attgcactcc agcctgggtg acaaagcaag actccatctc aaaaaaaaaa aaaaatcaag    2654 gaaggataaa aggaagttca gtattgtacc acacttggaa cttcctccat ttcttccatt    2714 ttagaaggat atgaacctgg aacttttgat gattctaagc cttaaactat caaaaagatc    2774 agggattgcc aatgcttcta atggcactgc aagtatatgc cataaccgtt ccctcctaaa    2834 agtgaaaaat gagagaaatt cagtattttc ccaggctcag catccagaag tctagctctg    2894 ggctggaaga aaagggtact aatatttagg gaagagatga gaataagtag tgggtggcag    2954 gagagggctg agctagtgcc tgctaacatt ttagttgtat cttggaaaga tttagcaaaa    3014 ataactcacc aggatagctg ctgaagagtt gatgaatggg agaagaaaga tgtttgagaa    3074 ataaagaaaa cagcagcctg caatacaata acttgccttt ttaatagttt tgattactct    3134 tgatacctac agcacaaatg ctggacctga atcagctctt caaggaccct agcacaaatg    3194 tcaactgatc acctctggga gagtagaaaa cttttttttt tttgagacga agtctcgctc    3254 tgttgcccag gctggagtgc agtggcacca tctcagctca ctgcagcgtc cgcctcttgg    3314
```

```
gttcaagtga ttctcctgcc ttgtcctcct gagtcgctgg tattacaggt gcctgccatc    3374
acacccagct aattttttgga gttctgatag agacaggggtt tctccatgtt ggccaggctt   3434
gtctcaagct cctgacctca agtgacctac ccacccttgg cctcccacag tgctggaagc    3494
cactgcacct ggctcagaat actttttttt ttgagatgca gtcttgctct catcacgcag    3554
gctggagtgc agtggcgtat ctcggctcac tgcgacctcc acctcccgag ttcaagcgat    3614
tctccttcct cagtccccca agtagcttgg attataggtg tgcgccacca cgtacagcta    3674 attttttgtat ttttagtaga gatggggttt cgccatgttg accaggctgg tctcaaaacg    3734
cctgacctca ggtgatccac ccacctcggc cccacaaagt gctaggatta caggtgtgag    3794
ccaccatgcc cggcccagaa tacttttttaa aagaagagca ggttagagga aagaaaaaaa    3854
ttgatgctga atgtggtgat gaaagcatgt ttctaaaatg ggaagcagat gcttaaagag    3914
gaaagactaa tctgggatttt tgccccattt ctctggtttt tcactcctat atttaattct    3974
cacaatcgtg tcgtcacata gtgcaaaaaa caaaattctt gtaaagtccc caggagtttta   4034 tgcttgggtg aaagttttag cctgagtatt ttcttcctct aaaaaaggtg ggaaatgaga    4094
cattgaggaa ttaacatata aatgtctgct atgggtttaa gagaactggc gtatttggaa    4154
tgcttcttac actaacactg tctcattgta aaatataaaa ccccttactc taactacatt    4214
tttattcctc tggtagtgtg gtatccaggc aacatatcac ttctgctatg taattctaag    4274
aattctcatt tctagagtac ctgagccaaa caaatacaca acggaagctg cagctgtatc    4334
atcactagca atttgctcat cattatttac tacctttgaa cctaaggttt cctgcctatg    4394
cttttgaaag caaaaatcag tctcctttgc atgaaaaaga gccttagatt tttaaacatg    4454
ttagttacca gaatgctaaa ataccagttg attacccaaa ttattttgga aatctatcca    4514
taatggaagt ctacaacaaa cacataaaac agattacact aagagctgag aaattcaaag    4574
gaactgaaga ttctgagaga taaactgttc aagtcttagc aatgatactg cacttctctt    4634
tgacaggttc tgggcttaag ttagaggccc tactggttcc aaaccatatt ccactgactt    4694
tgcaagtaaa ataaatttga ttctgaaata ggaaacaaaa aaaggagaaa taaccgaata    4754
gtagaagaaa aactgtttgt aggaagacga tgcagatgga atgatgtgga cattgagtaa    4814
ccatgtcaat aaaatatata aaccaaactt aaatttgtga aataaggaag ttggtacctt    4874
tgttgttaca gtgtataaaa acaatttcgg aactgctgtt gcaaaaagac atatatagtt    4934
ttgcttcctt ctggtgttaa gctgtttata tttcagtttc agttttaact tctaagttgc    4994
cttgtaattg ggactgtgtt tcagcatcac aaaaaccaaa tatttattat ggatgcatct    5054
gtatcagcaa ttaaaaaata aacaagtaaa agtgatactg taggagaagc tgaagctcaa    5114
aaaaaa                                                              5120
```

<210> SEQ ID NO 2
<211> LENGTH: 373
<212> TYPE: PRT
<213> ORGANISM: Homo sapiens

<400> SEQUENCE: 2

Met Ser Leu Leu Leu Leu Leu Leu Val Ser Tyr Tyr Val Gly Thr
1               5                   10                  15

Leu Gly Thr His Thr Glu Ile Lys Arg Val Ala Glu Glu Lys Val Thr
                20                  25                  30

Leu Pro Cys His His Gln Leu Gly Leu Pro Glu Lys Asp Thr Leu Asp
            35                  40                  45

Ile Glu Trp Leu Leu Thr Asp Asn Glu Gly Asn Gln Lys Val Val Ile
 50                  55                  60

Thr Tyr Ser Ser Arg His Val Tyr Asn Asn Leu Thr Glu Glu Gln Lys
 65                  70                  75                  80

Gly Arg Val Ala Phe Ala Ser Asn Phe Leu Ala Gly Asp Ala Ser Leu
                 85                  90                  95

Gln Ile Glu Pro Leu Lys Pro Ser Asp Glu Gly Arg Tyr Thr Cys Lys
             100                 105                 110

Val Lys Asn Ser Gly Arg Tyr Val Trp Ser His Val Ile Leu Lys Val
             115                 120                 125

Leu Val Arg Pro Ser Lys Pro Lys Cys Glu Leu Glu Gly Glu Leu Thr
         130                 135                 140

Glu Gly Ser Asp Leu Thr Leu Gln Cys Glu Ser Ser Ser Gly Thr Glu
145                 150                 155                 160

Pro Ile Val Tyr Tyr Trp Gln Arg Ile Arg Glu Lys Glu Gly Glu Asp
                 165                 170                 175

Glu Arg Leu Pro Pro Lys Ser Arg Ile Asp Tyr Asn His Pro Gly Arg
             180                 185                 190

Val Leu Leu Gln Asn Leu Thr Met Ser Tyr Ser Gly Leu Tyr Gln Cys
             195                 200                 205

Thr Ala Gly Asn Glu Ala Gly Lys Glu Ser Cys Val Val Arg Val Thr
         210                 215                 220

Val Gln Tyr Val Gln Ser Ile Gly Met Val Ala Gly Ala Val Thr Gly
225                 230                 235                 240

Ile Val Ala Gly Ala Leu Leu Ile Phe Leu Leu Val Trp Leu Leu Ile
                 245                 250                 255

Arg Arg Lys Asp Lys Glu Arg Tyr Glu Glu Glu Glu Arg Pro Asn Glu
             260                 265                 270

Ile Arg Glu Asp Ala Glu Ala Pro Lys Ala Arg Leu Val Lys Pro Ser
             275                 280                 285

Ser Ser Ser Ser Gly Ser Arg Ser Arg Ser Gly Ser Ser Thr
         290                 295                 300

Arg Ser Thr Ala Asn Ser Ala Ser Arg Ser Gln Arg Thr Leu Ser Thr
305                 310                 315                 320

Asp Ala Ala Pro Gln Pro Gly Leu Ala Thr Gln Ala Tyr Ser Leu Val
                 325                 330                 335

Gly Pro Glu Val Arg Gly Ser Glu Pro Lys Lys Val His His Ala Asn
             340                 345                 350

Leu Thr Lys Ala Glu Thr Thr Pro Ser Met Ile Pro Ser Gln Ser Arg
         355                 360                 365

Ala Phe Gln Thr Val
         370

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:forward
      primer

<400> SEQUENCE: 3
ttctctttga caggttctgg gc                                              22

<210> SEQ ID NO 4

-continued

```
<211> LENGTH: 21
<212> TYPE: DNA
<213> ORGANISM: Artificial Sequence
<220> FEATURE:
<223> OTHER INFORMATION: Description of Artificial Sequence:reverse
      primer

<400> SEQUENCE: 4
ggttggaacc agtagggcct c                                             21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:xs13 forward
      primer

<400> SEQUENCE: 5
agatccgcat gtcccttc                                                 18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:xs13 reverse
      primer

<400> SEQUENCE: 6
ccttgcgcat catggtgtt                                                19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:forward
      primer

<400> SEQUENCE: 7
ccccaggagt ttatgcttgg                                               20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:reverse
      primer

<400> SEQUENCE: 8
gcctggatac cacactacca g                                             21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:forward
      primer

<400> SEQUENCE: 9
attgtcagat cgttcattgc                                               20

<210> SEQ ID NO 10
<211> LENGTH: 20
```

```
<212> TYPE: DNA
<213> ORGANISM: Artificial Sequence
<220> FEATURE:
<223> OTHER INFORMATION: Description of Artificial Sequence:reverse
      primer

<400> SEQUENCE: 10
atggaacagg taaccagcat                                              20
```

METHODS FOR DIAGNOSIS AND THERAPY OF PANCREATIC CANCER AND COMPOSITION USEFUL THEREIN

BACKGROUND OF THE INVENTION

The present invention generally relates to methods for diagnosis of pancreatic cancer, compositions useful therefore and therapeutic methods for the treatment of pancreatic cancer.

Pancreatic cancer is a cancer type which is difficult to diagnose and to control and most of such cancers can grow very rapidly.

Neoplasms of the exocrine pancreas may arise from ductal, acinar and stromal cells. Eighty percent of pancreatic carcinomas are derived from ductal epithelium. 60% of these tumors are located in the head of the pancreas, 10% in the tail and 30% are located in the body of the pancreas or are diffuse (Warshau, A. L., and Fernandez-del, C. C., N. Engl. J. Med. 326 (1992) 4555-4565). Histologically, these tumors are graded as well as differentiated, moderately differentiated and poorly differentiated. Some tumors are classified as adenosquamous, mucinous, undifferentiated or undifferentiated with osteoblast-like giant cells (Gibson, J. B., and Sobin, L. H., Histological typing of tumors of the liver, biliary tract and pancreas, WHO, Geneva, 1978). Since the disease is asymptomatic in its early stages, because of the lack of any test for early diagnosis and due to its aggressive character with respect to metastasis locally and to visceral organs, this disease is associated with a dismal prognosis. Only 20% of the tumors are resectable and the survival benefit of approved chemotherapy regiments is rather poor (Kroep, J. R., et al., Ann. Oncol. 10, Suppl. 4 (1999) 234-238). Identification of new targets for early diagnosis of pancreatic tumors is therefore a challenge of paramount importance.

WO 02/08288 describes secreted and transmembrane polypeptides and nucleic acids encoding the same. FIG. 130 shows the polypeptide sequence of UKW.

SUMMARY OF THE INVENTION

It was surprisingly found that nucleic acids coding for polypeptide UKW are overexpressed specifically in pancreatic tumor cells, whereas expression is considerably lower in normal pancreatic cells or in tumor cells of other origin, e.g., breast cancer or colon cancer cells. Therefore, UKW is a valuable new target for specific diagnosis and therapy of pancreatic cancer.

According to one aspect of the present invention, a method for determining the presence or absence of pancreatic cancer in a patient comprises
  (i) obtaining a biological sample from a patient;
  (ii) detecting in the sample an amount of nucleic acid encoding UKW or an amount of polypeptide UKW; and
  (iii) comparing the amount of nucleic acid or polypeptide with a predetermined standard value indicating the decision line for tumor-induced or non-tumor-induced UKW expression or presence in the cell and therefrom determining the presence or absence of pancreatic cancer in the patient.

Preferably, the detection is performed by the use of a binding agent which binds to UKW nucleic acid or polypeptide. More preferably, the binding agent is a probe hybridizing under stringent conditions with UKW nucleic acid or an antibody, preferably a monoclonal antibody binding to UKW polypeptide, preferably to the extracellular domain.

According to another aspect of the present invention, there is provided a process for determining whether or not a test sample of tissue or fluid of a patient contains pancreatic tumor cells or is derived from pancreatic tumor cells, wherein the test sample and a second sample originating from non-pancreatic-tumor cells from the same individual or a different individual of the same species are used, which process comprises the following steps:
  (a) incubating each respective sample under stringent hybridization conditions with a nucleic acid probe which is selected from the group consisting of:
    (i) a nucleic acid sequence of SEQ ID NO: 1, or a fragment thereof;
    (ii) a nucleic acid sequence which is complementary to any nucleic acid sequence of (i);
    (iii) a nucleic acid sequence which hybridizes under stringent conditions with the sequence of (i); and
    (iv) a nucleic acid sequence which hybridizes under stringent conditions with the sequence of (ii); and
  (b) determining the approximate amount of hybridization of each respective sample with said probe, and
  (c) comparing the approximate amount of hybridization of the test sample to an approximate amount of hybridization of said second sample to identify whether or not the test sample contains a greater amount of the specific nucleic acid or mixture of nucleic acids than does said second sample.

According to a further aspect of the present invention, a method for the detection of pancreatic tumors, comprises
  a) incubating a sample of a patient suspected of suffering from pancreatic cancer, selected from the group of body fluid, of cells, or of a cell extract or cell culture supernatants of said cells, whereby said sample contains nucleic acids with a nucleic acid probe which is selected from the group consisting of
    (i) the nucleic acid shown in SEQ ID NO:1 or a nucleic acid which is complementary to said sequence, and
    (ii) nucleic acids which hybridize with one of the nucleic acids from (i) and
  b) detecting hybridization, preferably by means of a further binding partner of the nucleic acid of the sample and/or the nucleic acid probe or by X-ray radiography.

Both methods can also be performed by the use of antibodies, whereby the UKW polypeptide is detected by interaction between the antibody and the polypeptide.

The invention further provides a method for monitoring the progression of pancreatic cancer in the patient. In such a method, the amount of UKW nucleic acid or polypeptide in a biological sample (e.g., body fluids such as blood, cell lysates or a reverse transcript of an RNA sample) of a patient suffering from pancreatic cancer is determined at at least two different points in time and compared. From the change of the amount, information on the progression of said pancreatic cancer can be deduced.

The invention further comprises diagnostic kits comprising one or more oligonucleotide probes or primers for hybridization with UKW nucleic acid in a diagnostic assay using a sample obtained from a patient suffering from, or being suspected to have, pancreatic cancer.

The invention further comprises the use of antibodies against UKW polypeptide in a therapeutically effective amount in the treatment of pancreatic cancer. Preferably, the antibody is administered locally to the pancreas and especially preferably to the head of the pancreas.

In a further embodiment of the invention, the antibody against UKW polypeptide is administered to the patient in a therapeutically effective amount for the treatment of pancreatic cancer diseases and/or for preventing and/or inhibiting metastasis caused by pancreatic cancer diseases.

The above, and other objects, features and advantages of the present invention will become apparent from the following description read in conjunction with the accompanying drawings.

DETAILED DESCRIPTION OF THE INVENTION

As used herein, the term "UKW" means a nucleic acid encoding a polypeptide of SEQ ID NO:2, preferably the DNA sequence and the related mRNA sequence of SEQ ID NO:1 as well as the encoded polypeptide of SEQ ID NO:2. As UKW is a transmembrane receptor protein, the polypeptide is of outstanding interest for diagnosis and as an epitope for antibody binding the extracellular domain of UKW polypeptide is preferred. Therefore, it is preferred to direct the nucleic acid sample and probes to this region and especially to parts thereof which have low homology with other genes and polypeptides.

The UKW receptor is a transmembrane protein composed of 373 amino acids with a signal sequence of 18 amino acids. The receptor consists of an extracellular domain of 215 amino acids, a transmembrane domain of 23 amino acids and a cytoplasmic domain of 117 amino acids. The extracellular domains displays two immunoglobulin C2-type folds composed of 93 amino acids and 72 amino acids.

The phrase "nucleic acid or polypeptide" as used throughout this application refers to a nucleic acid or polypeptide having a UKW activity which is substantially free of cellular material or culture medium when produced by recombinant DNA techniques, or substantially free of chemical precursors or other chemicals when synthesized chemically. Such a nucleic acid is preferably free of sequences which naturally flank the nucleic acid (i.e. sequences located at the 5' and the 3' ends of the nucleic acid) in the organism from which the nucleic acid is derived.

"Nucleic acid probes and primers for UKW" as used herein means nucleic acid fragments useful for the detection of UKW nucleic acids by hybridization methods. Hybridization techniques and conditions are well-known to one skilled in the art. Such hybridization conditions are, for example, moderate stringent conditions including washing with a solution of 5×SSC, 0.5% SDS, 1.0 mmol/l EDTA, pH 8.0, followed by hybridization at 50-60° C. 5×SSC overnight, washing at room temperature for 40 minutes with 2×SSC containing 0.1% SDS and afterwards washing with 0.1×SSC, 0.1% SDS at 50° C. for 40 min with one change of fresh solution. It is also possible to use higher temperatures for hybridization (e.g. 65-70° C.) as high stringent hybridization conditions. The nucleic acid probes and primers usually consist of a UKW nucleic acid segment of at least about 50 contiguous positions most preferably of 200 to 300 nucleotides The optimization of the probes and primers can be performed according to the state of the art. There exists informatic software (http://www-genome.wi.mit.edu/genome_software/other/primer3.html) which is generally used for such probe and primer design. For high selectivity it is preferred to use relatively low salt and/or high temperature conditions, for example, a salt concentration from about 0.02 mol/l to about 0.15 mol/l and temperatures of from about 50° C. to about 70° C.

UKW polypeptides can be identified in diagnostic assays using specific probes and primers. Usually such methods include amplifying the target sequence in the sample by amplification methods such as the PCR method. Quantitative detection can be performed by PCR techniques, preferably by the use of quantitative RT-PCR using, e.g., the LIGHTCYCLER® of Roche Diagnostics GmbH, DE.

In a preferred embodiment of the invention the coding nucleic acid of the sample is amplified before the test, for example by means of the known PCR technique. Usually a derivatized (labeled) nucleic acid probe is used within the framework of nucleic acid diagnostics. This probe is contacted with a denatured DNA, RNA or RT-DNA from the sample which is bound to a carrier and in this process the temperature, ionic strength, pH and other buffer conditions are selected—depending on the length and composition of the nucleic acid probe and the resulting melting temperature of the expected hybrid—such that the labeled DNA or RNA can bind to homologous DNA or RNA (hybridization see also Wahl, G. M., et al., Proc. Natl. Acad. Sci. USA 76 (1979) 3683-3687). Suitable carriers are membranes or carrier materials based on nitrocellulose (e.g., Schleicher and Schull, BA 85, AMERSHAM HYBOND® C.), strengthened or bound nitrocellulose in powder form or nylon membranes derivatized with various functional groups (e.g.; nitro groups) (e.g., NYTRAN®; GENESCREEN®; AMERSHAM HYBOND® M; PALL BIODYNE®).

To determine whether a test sample contains pancreatic tumor cells, the approximate amount of hybridization of the nucleic acid with the target nucleic acid or nucleic acids is determined. The approximate amount of hybridization need not be determined quantitatively, although a quantitative determination is encompassed by the present invention. Typically, the approximate amount of hybridization is determined qualitatively, for example, by a sight inspection upon detecting hybridization. For example, if a gel is used to resolve labelled nucleic acid which hybridizes to target nucleic acid in the sample, the resulting band can be inspected visually. When performing a hybridization of isolated nucleic acid which is free from pancreatic tumor cells from an individual of the same species, the same protocol is followed. One can compare the approximate amount of hybridization in the test sample to the approximate amount of hybridization in the sample free from pancreatic tumor cells, to identify whether or not the test sample contains a greater amount of the target nucleic acid or nucleic acids than does the sample which is free from pancreatic tumor cells.

In a further method according to the invention no second sample is used. For the detection whether the expression of UKW gene is upregulated, the level of mRNA of UKW is compared with the level of mRNA of a standard gene (housekeeping gene (see, e.g., Shaper, N. L., et al., J. Mammary Gland Biol. Neoplasia 3 (1998) 315-324; Wu, Y. Y., and Rees, J. L., Acta Derm. Venereol. 80 (2000) 2-3) of the cell, preferably by RT-PCR.

As is shown in accordance with the present invention, the UKW nucleic acid is expressed in a greater amount in a pancreatic tumor sample than in a sample free from pancreatic_tumor cells and/or in a greater amount than a housekeeping gene. A test sample containing pancreatic tumor cells will have a greater amount of the UKW nucleic acid than does a sample which is free from pancreatic tumor cells. To identify a test sample as containing upregulated UKW nucleic acid, i.e., wherein the cells are pancreatic tumor cells or are tumor cells of a mammary carcinoma, it is preferable that the test sample have an approximate amount of UKW nucleic acid which is appreciably greater than the approximate amount in a sample free of pancreatic tumor cells. For example, a test sample having an upregulated UKW gene may have approximately 15- to approximately 60-fold increased amount of UKW gene than a sample free of pancreatic tumor cells or an at least 3-fold greater amount of UKW mRNA than mRNA of a housekeeping gene like glycerolaldehyde-3-phosphate dehydrogenase (GAPDH) or porphobilinogen deaminase.

Methods of hybridization of a probe and a nucleic acid are known to a person skilled in the art and are described, for example, in WO 89/06698, EP-A 0 200 362, U.S. Pat. No. 2,915,082, EP-A 0 063 879, EP-A 0 173 251, EP-A 0 128 018.

Hybridizing DNA or RNA is then detected by incubating the carrier with an antibody or antibody fragment after thorough washing and saturation to prevent unspecific binding. The antibody or the antibody fragment is directed towards the substance incorporated during hybridization to the nucleic acid probe. The antibody is in turn labeled. However, it is also possible to use a directly labeled DNA. After incubation with the antibodies it is washed again in order to only detect specifically bound antibody conjugates. The determination is then carried out according to known methods by means of the label on the antibody or the antibody fragment.

The detection of the expression can be carried out for example as:
  in situ hybridization with fixed whole cells, with fixed tissue smears,
  colony hybridization (cells) and plaque hybridization (phages and viruses),
  Southern hybridization (DNA detection),
  Northern hybridization (RNA detection),
  serum analysis (e.g., cell type analysis of cells in the serum by slot-blot analysis),
  after amplification (e.g., PCR technique).

The nucleic acids according to the invention are hence valuable markers in the diagnosis and characterization of pancreatic tumors.

According to the invention inhibitors for the expression of UKW (e.g., antibodies or antisense nucleotides) can be used to inhibit pancreatic tumor progression in vivo.

The invention further provides methods for the identification and isolation of antagonists of UKW or inhibitors for the expression of UKW (e.g., antibodies and antisense nucleotides). Such antagonists or inhibitors can be used to inhibit pancreatic tumor progression and cause massive apoptosis of pancreatic tumor cells in vivo.

According to the invention there are provided methods for identifying and isolating of UKW antagonists which have utility in the treatment of cancer. These methods include methods for modulating the expression of the polypeptides according to the invention, methods for identifying UKW antagonists which can selectively bind to the proteins according to the invention, and methods of identifying UKW antagonists which can modulate the activity of said polypeptides. The methods further include methods for modulating, preferably inhibiting, the transcription of UKW gene to mRNA. These methods can be conducted in vitro or in vivo and may make use of and establish cell lines and transgenic animal models of the invention.

A UKW antagonist is defined as a substance or compound which decreases or inhibits the biological activity of UKW, a polypeptide and/or inhibits the transcription or translation of UKW gene. In general, screening procedures for UKW antagonists involve contacting candidate substances with host cells in which invasiveness is mediated by expression of UKW under conditions favorable for measuring UKW activity.

UKW activity may be measured in several ways. Typically, the activation is apparent by a change in cell physiology, such as increased mobility and invasiveness in vitro, or by a change in the differentiation state, or by a change in cell metabolism leading to an increase of proliferation.

The UKW polypeptides can be produced by recombinant means or synthetically. Non-glycosylated UKW polypeptide is obtained when it is produced recombinantly in prokaryotes. With the aid of the nucleic acid sequences provided by the invention it is possible to search for the UKW gene or its variants in genomes of any desired cells (e.g. apart from human cells, also in cells of other mammals), to identify these and to isolate the desired gene coding for the UKW proteins. Such processes and suitable hybridization conditions are known to a person skilled in the art and are described, for example, by Sambrook et al., Molecular Cloning: A Laboratory Manual (1989) Cold Spring Harbor Laboratory Press, New York, USA, and Hames, B. D., Higgins, S. G., Nucleic Acid Hybridisation—A Practical Approach (1985) IRL Press, Oxford, England. In this case the standard protocols described in these publications are usually used for the experiments.

With the aid of such nucleic acids coding for a UKW polypeptide, the polypeptide according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as, e.g., E. coli as a prokaryotic host cell or Saccharomyces cerevisiae, teratocarcinoma cell line PA-1, sc 9117 (Büttner, R., et al., Mol. Cell. Biol. 11 (1991) 3573-3583), insect cells, CHO or COS cells as eukaryotic host cells and the transformed or transduced host cells are cultured under conditions which allow expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary if it is not found in soluble form in the cell culture.

UKW polypeptide or fragments thereof can be purified after recombinant production by affinity chromatography using known protein purification techniques, including immunoprecipitation, gel filtration, ion exchange chromatography, chromatofocusing, isoelectric focussing, selective precipitation, electrophoresis, or the like and can be used for the generation of antibodies against UKW.

The invention further comprises recombinant expression vectors which are suitable for the expression of UKW, recombinant host cells transfected with such expression vectors, as well as a process for the recombinant production of a protein which is encoded by the UKW gene.

Antibodies against UKW can be produced according to the methods known in the state of the art. For example, monoclonal or polyclonal antibodies can be produced using a polypeptide comprising about 10 to 100 amino acids of the UKW polypeptide sequence. Suitable polypeptides derived from UKW include preferably amino acids from the extracellular domain, preferably amino acids 70-80, 99-113, 120-140 and 167-182.

The resulting antibodies can be screened for the ability to bind to UKW using standard techniques such as enzyme-linked immunoabsorbent assays. Methods for identifying antigen epitopes and for the production of antibodies are described, for example, in Mole, "Epitope Mapping", In: Methods in Molecular Biology, Vol. 10, Manson (ed.), pages 105-116, The Humana Press, Inc., 1992; Price, "Production and Characterization of Synthetic Peptide-Derived Antibodies", In: Monoclonal Antibodies: Production, Engineering, and Clinical Application, Ritter and Ladyman (eds.), pp. 60-84, Cambridge University Press, 1995; Morris (ed.), Epitope Mapping Protocols 25, Humane Press, Inc., 1996; and Coligan et al. (eds.), Current Protocols in Immunology, pp. 9.3.1-9.3.5 and pp. 9.4.1-9.4.11, John Wiley & Sons, 1997.

Antibodies which are useful according to the invention, especially for therapeutic purposes, can be identified by reducing the proliferation and invasive potential of pancreatic tumor cells. For this purpose, pancreatic tumor cells or a pancreatic tumor cell line, preferably cell line SUIT-2 607 are treated with an antibody against UKW and proliferation and invasive potential are measured by Cell Proliferation Reagent WST-1 (a tetrazolium salt reagent, Roche Diagnostics GmbH, DE) and MATRIGEL™ invasion assay (BDS Biosciences, www.bdbiosciences.com).

Anti-UKW antibodies can be derived from any animal species or are chimeric or humanized antibodies. Especially preferred are human antibodies. Human monoclonal antibodies are obtained, for example, from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green, L. L., et al., Nat. Genet. 7 (1994) 13-21; Lonberg, N., et al., Nature 368 (1994) 856-859; and Taylor, L. D., et al., Int. Immun. 6 (1994) 579-591.

Monoclonal antibodies can be isolated and purified from hybridoma cultures by a variety of well-established techniques. Such isolation techniques include affinity chromatography with PROTEIN-A SEPHAROSE®, size-exclusion chromatography, and ion-exchange chromatography (see, for example, Coligan at pages 2.7.1-2.7.12 and pages 2.9.1-2.9.3; Baines et al., "Purification of Immunoglobulin G (lgG)", In: Methods in Molecular Biology, Vol. 10, pages 79-104, The Humana Press, Inc., 1992).

The antibodies can be used for immunoassays according to the invention. Detection can be performed by contacting a biological sample with an antibody, and then contacting the biological sample with a detectably labeled molecule, which binds to the antibody. The antibody can be conjugated with avidin/streptavidin (or biotin) and the detectably labeled molecule can comprise biotin (or avidin/streptavidin). Numerous variations of this basic technique are well-known to those of skill in the art. Alternatively, an antibody can be conjugated with a detectable label to form an immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art and are described in more detail below.

Preferably, the antibodies according to the invention can be used for the treatment of a patient suffering from a pancreatic tumor. The advantage of such a therapy with a pharmaceutical composition comprising an anti-UKW antibody can be demonstrated in an in vivo pancreas tumor model. Such a model is described by Alves, F., et al., Pancreas 23 (2001) 227-235. This in vivo model comprises an orthotopic transplant model for pancreatic ductal adenocarcinoma in severe combined immunodeficient (SCID) mice. Generally, the dosage of administered anti-UKW antibodies will vary depending upon such factors as the subject's age, weight, height, sex, general medical condition and previous medical history. As an illustration, anti-UKW antibodies compositions can be administered at low protein doses, such as 20 to 100 milligrams protein per dose, given once, or repeatedly. Alternatively, the antibodies can be administered in doses of 30 to 90 milligrams protein per dose, or 40 to 80 milligrams protein per dose, or 50 to 70 milligrams protein per dose.

Administration of antibody components to a subject can be preferably intravenous, intramuscular, by perfusion through a regional catheter, preferably directly or vicinal to the pancreas organ. The administration may be by continuous infusion or by single or multiple boluses.

A pharmaceutical composition comprising an anti-UKW antibody, can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those skilled in the art. See, for example, Gennaro (ed.), Remington's Pharmaceutical Sciences, 19th edition, Mack Publishing Company, 1995.

For purposes of therapy, anti-UKW antibodies and a pharmaceutically acceptable carrier are administered to a patient in a therapeutically effective amount. A combination of the antibody and a pharmaceutically acceptable carrier is said to be administered in a "therapeutically effective amount" if the amount administered is physiologically significant.

A pharmaceutical composition comprising anti-UKW antibodies is preferably established in liquid injectable or infusable form.

The following examples, references, sequence listing and figures are provided to aid the understanding of the present invention, the true scope of which is set forth in the appended claims. It is understood that modifications can be made in the procedures set forth without departing from the spirit of the invention.

Pancreatic tumor cell lines:

Suit-2 007[1]
MiaPaca-2, ATCC CRL 1420
AsPC1, ATCC CRL 1682
BxPC-3, ATCC CRL 1687
Capan-1, ATCC HTB79
IMIM-PC-1[3]
IMIM-PC-2[3]
Panc-1, ATCC CRL 1469
Suit-2 028[1]
Capan-2, ATCC HTB80
Patu 8902[2]
Patu 8988s[2]
Patu 8988t[2]

Mammary tumor cell lines:

BT-549, ATCC HTB122
Hs578T, ATCC HTB126
MCF-10A, ATCC CRL 10317
MCF-12A, ATCC CRL 10782
MDA-MB-436[4]
MDA-MB-231, ATCC 45518
MDA-MB-435, ATCC 45526
MDA-MB-157, ATCC HTB24
BT-20, ATCC HTB19
BT-483, ATCC HTB 121
CAMA-1, ATCC HTB-21
Du4475, DSM ACC427
MCF-7, ATCC HTB22
MDA-MB-175, ATCC 45516
MDA-MB-361, ATCC HTB27
MDA-MB-453, DSM ACC65
SK-BR-3, ATCC 45520
T47D, ATCC HTB133
UCAA-812[4]
ZR-75-1, ATCC CRL 1500
ZR-75-30, ATCC CRL 1504

[1]Taniguchi, S., et al., Clin. Exp. Metastasis 10 (1992) 259-266
[2]Elsasser, H. P., et al., Virchows Arch. B Cell Pathol. Incl. Mol. Pathol. 64 (1993) 201-207
[3]Wenger, C., et al., Oncogene 18 (1999) 1073-1080
[4]Tong, D., et al., Breast Cancer Res. Treat. 56 (1999) 91-97

EXAMPLE 1

Materials and Methods

Figure 1:
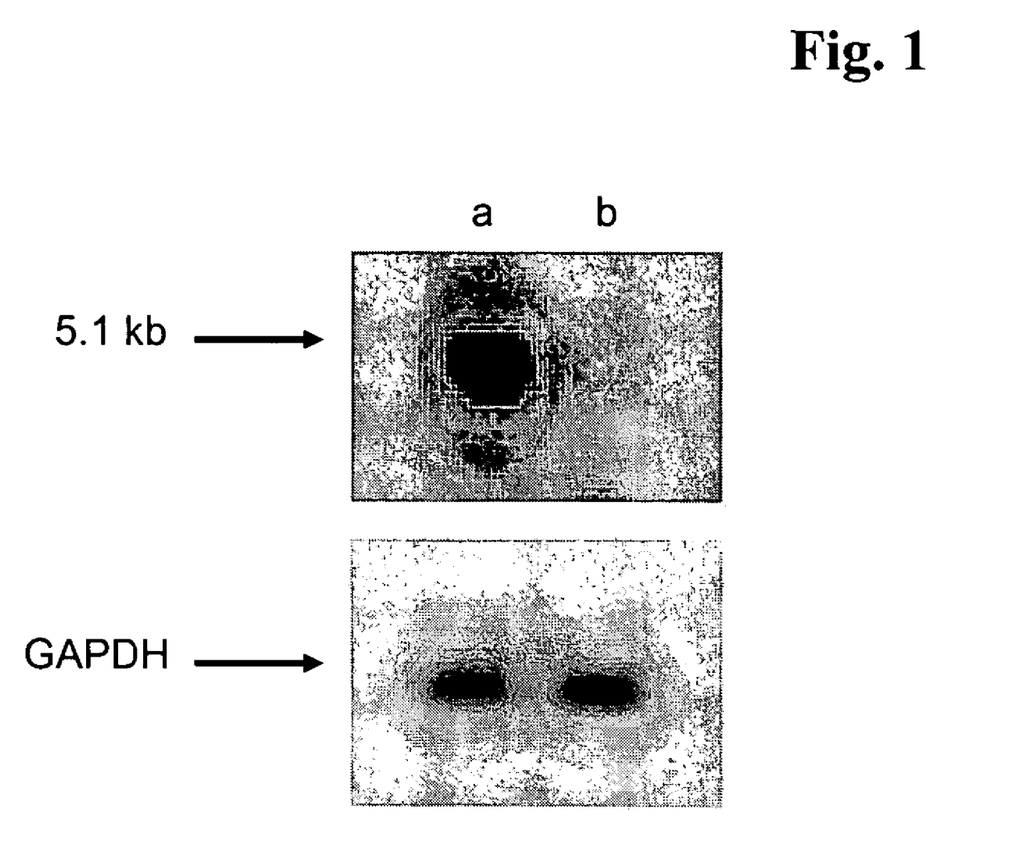
FIG. 1 Differential expression of UKW mRNA in pancreatic tumor cell lines SUIT-2 007 and SUIT-2 028 analyzed by Northern blot analysis.
(a: pancreatic tumor cell line SUIT-2 007; b: pancreatic tumor cell line SUIT-2 028)

Northern Blot:

10 μg of total RNA from SUIT-2 007 and SUIT-2 028 cell lines were loaded side by side on a denaturing 1% agarose formaldehyde gel and size-separated by electrophoresis. Blotting to BRIGHTSTAR-PLUS™ positively charged nylon membrane was performed by capillary downward transfer. After UV-crosslinking (STRATAGENE UV STRATALINKER® 2400) the blot was hybridized. The RT-PCR product was labeled with $\alpha$-[$^{32}$P]dATP to a specific activity of $2\times10^9$ cpm/μg using the STRIP-EZ™ DNA Kit (Ambion Inc., Austin, Tex.). Pre-hybridization (30 mm) and hybridization (over-night) with the radioactive probe was performed in EXPRESSHYB™ Hybridization Solution (Clontech, Palo Alto, Calif., USA) at 68° C. The membrane was washed in solution 1 (2×SSC, 0.05% SDS) at room temperature for 30-40 mm with continuous agitation and several replacements of the wash solution 1 followed by a washing step with solution 2 (0.1×SSC, 0.1% SDS) at 50° C. for 40 min with one change of fresh solution. The membrane was then exposed to CRONEX®, Medical X-Ray Films (Sterling Diagnostic Imaging Inc., USA) at—70° C. for 2 h. Equal loading and transfer of mRNA to the membrane was assessed by rehybridizing the blot with $\alpha$-[$^{32}$P]dATP-labeled GAPDH cDNA probe.

Multiple Tissue Expression Array (MTE™)

The blot was hybridized with an $\alpha$-[$^{32}$P]dATP labeled probe derived from UKW cDNA according to the instructions of the manufacturer and exposed to X-ray film at −70° C. for 62 h.

TAQMAN®-PCR

Figure 3:
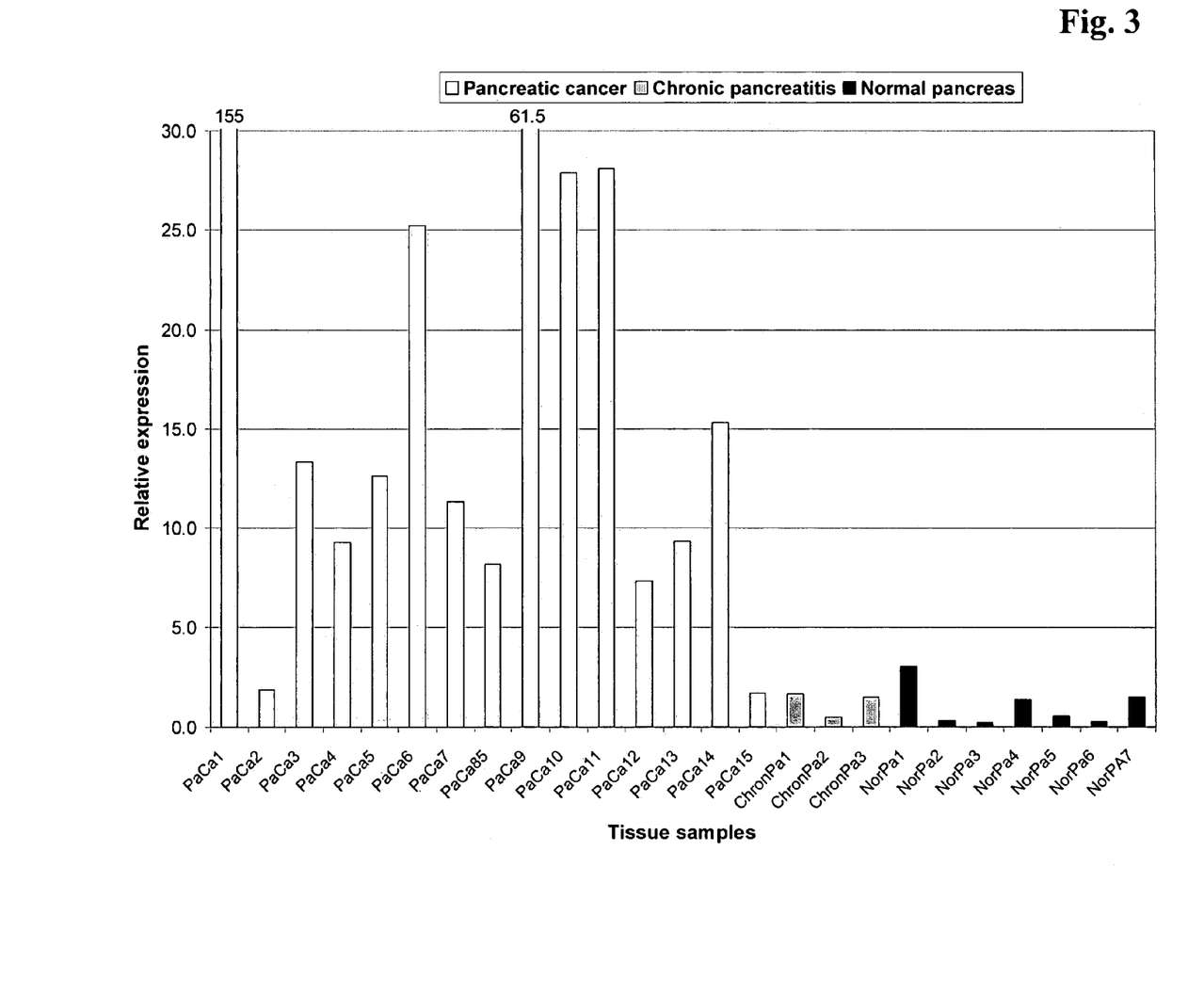
FIG. 3 Relative expression (TAQMAN® quantitative PCR) (Roche) of mRNA in samples derived from adenocarcinomas of the pancreas (PaCa), chronic pancreatitis (ChronPa) and normal pancreatic tissues (N or PA).
Figure 4:
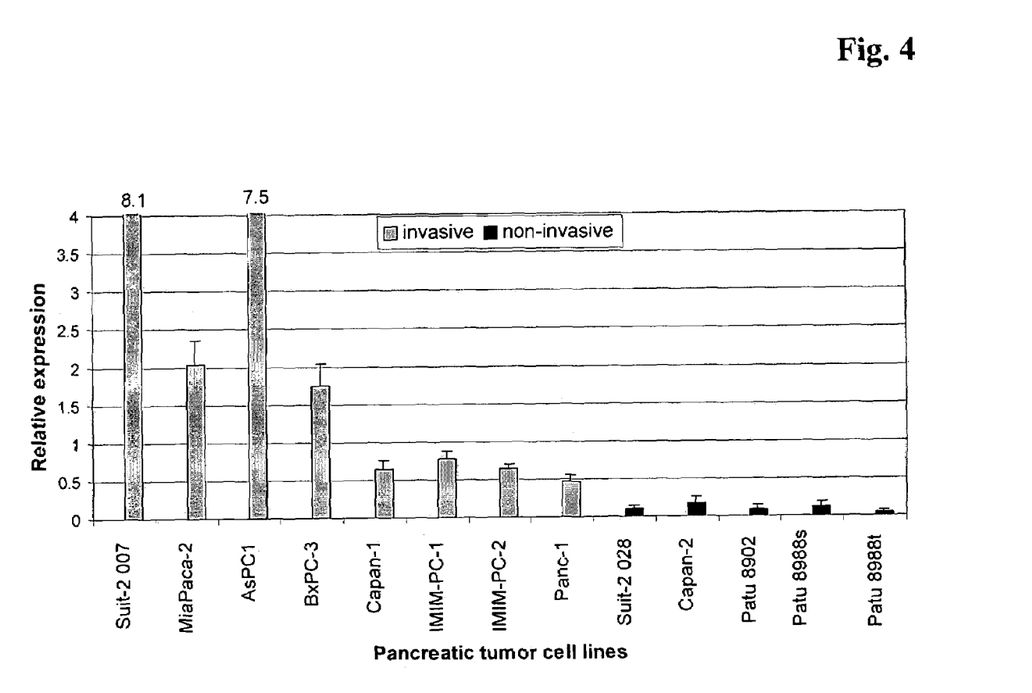
FIG. 4 Relative expression of UKW mRNA in invasive and non-invasive pancreatic tumor cell lines.
Figure 5:
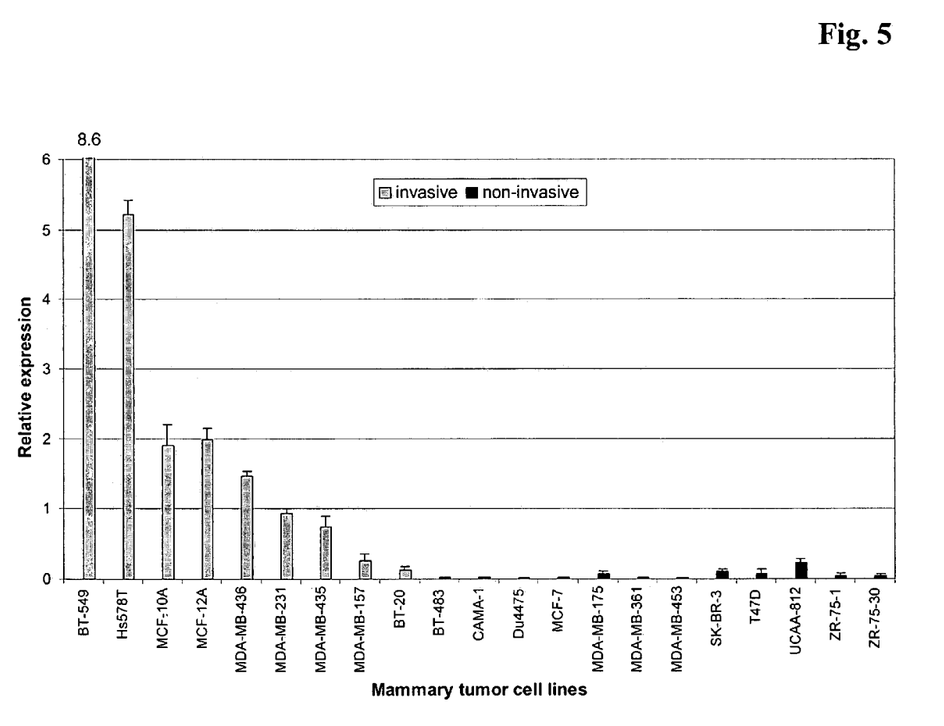
FIG. 5 Relative expression of UKW mRNA in invasive and non-invasive mammary tumor cell lines.

Real-time quantitative PCRs were performed with the TAQMAN® technology and the ABI PRISM® 7700 apparatus (Applied Biosystems, Foster City, Calif.). 10 μg total RNA isolated from frozen adenocarcinomas of the pancreas, chronic pancreatitis and normal pancreatic tissues were used for reverse transcriptase reactions in a volume of 20 μl. The PCRs were then carried out by mixing 200 ng cDNA with 4 μl of 10×SYBR®- Green buffer, 3 mM $MgCl_2$, 1 mM dNTDs, 0.2 units Uracil-N Glycosylase, 1 unit AMPLITAQ® Gold, 4 μl primer mix (300 nM each primer: forward 5'TTCTCTTTGACAGGTTCTGGGC3' (SEQ ID NO:3); reverse 5'GGTTGGAACCAGTAGGGCCT3') (SEQ ID NO:4) in a final volume of 40 μl. PCR primers were designed to generate a DNA fragment of 50 bp using the PRIMER EXPRESS® Software (PE Biosystems, CA, USA). The amplification cycles were as follows: 2 min at 50° C. followed by 10 min at 95° C. and 40 amplification cycles (95° C. for 15 sec and 60° C. for 60 sec). These experiments were performed twice. The results were calculated by subtraction of gene UKW and housekeeping gene RNA steady-state levels for each sample. Each value was divided by the averaged steady-state level of UKW mRNA of three healthy tissues. Ratios were squared and a reciprocal value was formed.

Primers:

```
xs13for:   5'AGATCCGCATGTCCCTTC3';    (SEQ ID NO:5)

xs13rev:   5'CCTTGCGCATCATGGTGTT3'.   (SEQ ID NO:6)
```

LIGHTCYCLER®-PCR

LIGHTCYCLER® quantitative PCR was performed with a LIGHTCYCLER® (Roche Molecular Biochemicals, Mannheim, Germany) in LIGHTCYCLER® capillaries using a commercially available master mix containing Taq DNA polymerase, SYBR®-Green I, deoxyribonucleoside triphosphates (LIGHTCYCLER® DNA master SYBR®-Green I, Roche Molecular Biochemicals). After addition of primers (forward 5'CCCCAGGAGTTTATGCTTGG3' (SEQ ID NO:7); reverse 5'GCCTGGATACCACACTACCAG3' (SEQ ID NO:8); final concentration: 0.5 μM), $MgCl_2$ (3 mM) and template DNA to the master mix, 37 cycles of denaturation (95° C. for 1 sec), annealing (58° C. for 5 sec) and extension (72° C. for 8 sec) were performed. All temperature transition rates were set to 20° C. per sec. After completion of PCR amplification, melting curve analysis was performed. For this procedure, PCR products were denatured at 95° C., annealed at 65° C., and gradually heated to 95° C. SYBR®-Green I fluorescence was monitored stepwise every 0.1° C. The melting curve was analyzed by visual inspection, amplified UKW gene rearranged structures were melting at 85-88° C. To control for primer dimer formation a control without template DNA ('water control') was included in each experiment. A small peak was usually visible at 78° C., which could be differentiated from the peak caused by the specific amplification product at 85-88° C. Calibration curve for calnexin was generated using serial dilutions (1:10, 1:50 and 1:80) of cDNA from pancreatic cancer cell line Suit-2 007. The relative amounts of UKW cDNA and calnexin were determined based on a calibration curve. Relative expression of gene UKW was calculated as a normalized value generated by dividing the steady-state levels of gene UKW and calnexin for each sample. Calnexin forward primer 5'ATTGTCA-GATCGTTCATTGC3' (SEQ ID NO:9); reverse primer 5'ATGGAACAGGTAACCAGCAT3' (SEQ ID NO:10).

EXAMPLE 2

Production of Antibodies Against UKW Polypeptide

For immunization the peptides aa 167-182 and aa 306-320 (SEQ ID NO:2) were synthesized and coupled to a carrier molecule. Immunization of two rabbits with the mix of the peptides.

Standard Immunization Protocol (for Rabbits):

| Day 0 | Taking of pre-immune serum followed by the first immunization |
| Day 14 | Second immunization |
| Day 28 | Third immunization |
| Day 38 | Blood sampling |
| Day 56 | Fourth immunization |
| Day 66 | Blood sampling |
| Day 80 | Complete bleeding |

The antiserum recovered was purified by affinity chromatography.

LIST OF REFERENCES

Alves, F., et al., Pancreas 23 (2001) 227-235
Ausubel I., Frederick M., Current Protocols in Mol. Biol. (1992), John Wiley and Sons, New York
Baines et al., "Purification of Immunoglobulin G (IgG)", In: Methods in Molecular Biology, Vol. 10, pages 79-104, The Humana Press, Inc., 1992
Büttner, R., et al., Mol. Cell. Biol. 11 (1991) 3573-3583
Coligan et al. (eds.), Current Protocols in Immunology, pp. 9.3.1-9.3.5 and pp. 9.4.1-9.4.11, John Wiley & Sons, 1997
Elsasser, H. P., et al., Virchows Arch. B Cell Pathol. Incl. Mol. Pathol. 64 (1993) 201-207
EP-A 0 063 879
EP-A 0 128 018
EP-A 0 173 251
EP-A 0 200 362
Gennaro (ed.), Remington's Pharmaceutical Sciences, 19th edition, Mack Publishing Company, 1995
Gibson, J. B., and Sobin, L. H., Histological typing of tumors of the liver, biliary tract and pancreas, WHO, Geneva, 1978
Green, L. L., et al., Nat. Genet. 7 (1994) 13-21
Hames, B. D., Higgins, S. G., Nucleic Acid Hybridisation—A Practical Approach (1985) IRL Press, Oxford, England
Kroep, J. R., et al., Ann. Oncol. 10, Suppl. 4 (1999) 234-238
Lonberg, N., et al., Nature 368 (1994) 856-859
Mole, "Epitope Mapping", In: Methods in Molecular Biology, Vol. 10, Manson (ed.), pages 105-116, The Humana Press, Inc., 1992
Morris (ed.), Epitope Mapping Protocols 25, Humane Press, Inc., 1996
Price, "Production and Characterization of Synthetic Peptide-Derived Antibodies", In: Monoclonal Antibodies: Production, Engineering, and Clinical Application, Ritter and Ladyman (eds.), pp. 60-84, Cambridge University Press, 1995
Sambrook et al., Molecular Cloning: A Laboratory Manual (1989) Cold Spring Harbor Laboratory Press, New York, USA
Shaper, N. L., et al., J. Mammary Gland Biol. Neoplasia 3 (1998) 315-324
Taniguchi, S., et al., Clin. Exp. Metastasis 10 (1992) 259-266
Taylor, L. D., et al., Int. Immun. 6 (1994) 579-591
Tong, D., et al., Breast Cancer Res. Treat. 56 (1999) 91-97
U.S. Pat. No. 2,915,082
Wahl, G. M., et al., Proc. Natl. Acad. Sci. USA 76 (1979) 3683-3687
Warshau, A. L., and Fernandez-del, C. C., N. Engl. J. Med. 326 (1992) 4555-4565
Wenger, C., et al., Oncogene 18 (1999) 1073-1080
WO 02/08288
WO 89/06698
Wu, Y. Y., and Rees, J. L., Acta Derm. Venereol. 80 (2000) 2-3

We claim:

1. A method for determining the presence or absence of pancreatic cancer in a patient comprising:
   (i) obtaining a biological sample from said patient;
   (ii) detecting, in the sample, mRNA which is capable of being used in the production of the sequence consisting of SEQ ID NO: 1; and
   (iii) comparing the amount of mRNA detected with a predetermined standard value indicating the decision line for tumor-induced or non-tumor-induced expression or presence of mRNA which is capable of being used in the production of the sequence consisting of SEQ ID NO: 1 and therefrom determining the presence or absence of pancreatic cancer in the patient.

2. A process for determining whether or not a test sample of tissue or fluid of a patient contains pancreatic tumor cells wherein the test sample and a second sample originating from non-pancreatic-tumor cells from the same individual or a different individual of the same species are used,
   wherein the samples are assayed for mRNA which is capable of being used in the production of the sequence consisting of SEQ ID NO: 1 with a probe selected from the group consisting of:
   (i) the nucleic acid consisting of SEQ ID NO:1 or a fragment thereof, said fragment consisting of a nucleotide sequence comprising 50 contiguous nucleotides of SEQ ID NO:1; and
   (ii) a nucleic acid consisting of a polynucleotide which is 100% complementary to said nucleic acid consisting of SEQ ID NO:1 or said fragment thereof;
   wherein determination of approximately 15 fold to approximately 60 fold greater level of mRNA which is capable of being used in the production of the sequence consisting of SEQ ID NO: 1 in the test sample compared to the level of mRNA which is capable of being used in the production of the sequence consisting of SEQ ID NO: 1 in the second sample, indicates that said test sample contains pancreatic cancer cells.

3. A process according to claim 2 wherein said nucleic acid probe is the nucleic acid sequence consisting of SEQ ID NO: 1, or a fragment thereof, said fragment comprising 50 contiguous nucleotides of SEQ ID NO: 1.

4. A process according to claim 2 wherein said nucleic acid probe is the nucleic acid sequence consisting of SEQ ID NO: 1.

5. A process according to claim 2 wherein said nucleic acid probe is the nucleic acid shown in SEQ ID NO:1 or a nucleic acid which is 100% complementary to said sequence.

* * * * *